(12) United States Patent
Bonzon et al.

(10) Patent No.: US 10,352,954 B2
(45) Date of Patent: Jul. 16, 2019

(54) SENSING TIP WITH ELECTRICAL IMPEDANCE SENSOR

(71) Applicant: Ecole Polytechnique Fédérale de Lausanne (EPFL), Lausanne (CH)

(72) Inventors: David Vincent Bonzon, Mont-Pélerin (CH); Georges Henri Muller, Lausanne (CH); Philippe Renaud, Switzerland (CH); Yann Barrandon, Echandens-Denges (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 2 days.

(21) Appl. No.: 15/029,637

(22) PCT Filed: Oct. 14, 2014

(86) PCT No.: PCT/IB2014/065306
§ 371 (c)(1),
(2) Date: Apr. 15, 2016

(87) PCT Pub. No.: WO2015/056176
PCT Pub. Date: Apr. 23, 2015

(65) Prior Publication Data
US 2016/0238626 A1  Aug. 18, 2016

(30) Foreign Application Priority Data

Oct. 15, 2013  (WO) .................. PCT/IB2013/059372

(51) Int. Cl.
*G01N 35/10*  (2006.01)
*G01N 15/02*  (2006.01)
(Continued)

(52) U.S. Cl.
CPC .............. *G01N 35/10* (2013.01); *B01L 3/021* (2013.01); *B01L 3/0275* (2013.01);
(Continued)

(58) Field of Classification Search
CPC ............. B01L 3/021; B01L 2300/0645; B01L 2300/0636; B01L 2200/10; B01L 3/0275;
(Continued)

(56) References Cited

U.S. PATENT DOCUMENTS 2,656,508 A   10/1953  Coulter
3,714,565 A   1/1973  Coulter et al.
(Continued)

FOREIGN PATENT DOCUMENTS

EP   0 494 735 B1   11/1995
EP   0494735 B1    11/1995
(Continued)

OTHER PUBLICATIONS

Aug. 2, 2016 International Search Report issued in International Application No. PCT/IB2014/065306.
(Continued)

*Primary Examiner* — Rebecca M Fritchman
(74) *Attorney, Agent, or Firm* — Nixon & Vanderhye P.C.

(57) ABSTRACT

A sensing tip including a pipette tip having a cavity which communicates with an external environment of the pipette tip through an aperture located at a distal end of the pipette tip, and an impedance sensor having a sensing area including at least two electrodes located respectively outside and inside the pipette tip, wherein the sensing area is arranged within the aperture.

16 Claims, 3 Drawing Sheets

(51) Int. Cl.
*B01L 3/02* (2006.01)
*G01N 15/12* (2006.01)
*G01N 15/10* (2006.01)

(52) U.S. Cl.
CPC ..... *G01N 15/0266* (2013.01); *G01N 15/1218* (2013.01); *B01L 2200/10* (2013.01); *B01L 2300/0636* (2013.01); *B01L 2300/0645* (2013.01); *G01N 2015/1087* (2013.01); *G01N 2015/1254* (2013.01); *G01N 2035/1048* (2013.01); *G01N 2035/1062* (2013.01)

(58) Field of Classification Search
CPC ............... G01N 15/1218; G01N 35/10; G01N 2015/1254; G01N 2035/1062
USPC ......................................................... 436/150
See application file for complete search history.

(56) References Cited

U.S. PATENT DOCUMENTS

| 2010/0199788 | A1  | 8/2010 | Ayliffe et al. |
| 2011/0162439 | A1* | 7/2011 | Ayliffe .................. G01N 15/12 73/61.71 |

FOREIGN PATENT DOCUMENTS

| EP | 1 266 607 A2 | 12/2002 |
| EP | 126607 A2 | 12/2002 |
| EP | 2 177 916 A1 | 4/2010 |
| WO | 01/11338 A1 | 2/2001 |
| WO | WO0111338 A1 | 2/2001 |
| WO | 03/048728 A2 | 6/2003 |
| WO | WO03048728 A2 | 6/2003 |
| WO | 2005/121780 A2 | 12/2005 |
| WO | WO2005121780 A2 | 12/2005 |
| WO | 2010/093998 A2 | 8/2010 |
| WO | WO2010093998 A2 | 8/2010 |
| WO | 2010/126459 A1 | 11/2010 |
| WO | WO2010126459 A1 | 11/2010 |

OTHER PUBLICATIONS

Aug. 2, 2016 Written Opinion issued in International Application No. PCT/IB2014/065306.
Jan. 30, 2015 International Search Report issued in International Application No. PCT/IB2014/065306.
Jan. 30, 2015 Written Opinion issued in International Application No. PCT/IB2014/065306.
Mar. 13, 2018 Communication pursuant to Article 94(3) EPC issued in European Application No. 14802157.9.
International Search Report of PCT/IB2016/052177 dated Aug. 2, 2016
Written Opinion of the International Search Authority dated Aug. 2, 2016.
International Search Report (ISR) dated Jan. 30, 2015.
Written Opinion of the International Search Authority dated Jan. 30, 2015.

* cited by examiner

SENSING TIP WITH ELECTRICAL IMPEDANCE SENSOR

The present application is a U.S. national stage application of PCT/IB2014/065306 filed on Oct. 14, 2014 that designated the U.S., and claims foreign priority to the Patent Cooperation Treaty application PCT/IB2013/059372 filed on Oct. 15, 2013, the contents of both documents being herewith incorporated by reference in their entirety.

FIELD OF INVENTION

The present invention relates to the sensing of particles within a fluid, in particular to the detection of particles such as cells within a liquid.

PRIOR ART

Pipettes are extensively used in laboratory to precisely handle fluids. They usually are made of a fluidic pump actuated with a plunger controlling the volume of handled fluid. The tip of the pipette that is in contact with the fluid is made of a single-use plastic material. Although standard pipettes are very precise to control the volume of handled liquid, they do not provide information or control about the particles contained in the fluid.

A method to detect particles in a fluid was first described in the Coulter counter design (U.S. Pat. No. 2,656,508A). This method allows for characterizing dielectric particles in a fluid in term of number and size. However, this prior art does not describe an embodiment suited for integration on a pipette tip.

Later the coupling of a Coulter counter to a pipette tip was proposed by Gascoyne et al. (WO2005/121780). This allows for characterizing and measuring particles contained in a fluid. However, there is no description of the sensor implementation.

An implementation for the sensor in the tip was later described by Ayliffe et al. (US2010/0199788A1). This tip may be embodied to count particles, verify sample integrity, monitor flow rate and confirm an inspired volume. The tip is made of a plurality of layers comprising a fluid path where particles flow. The sensor is located in the fluid path. There is a dead volume in the fluid path in between the tip extremity and the sensor. With this design, it is required to sample a sufficient number of particles to fill the dead volume. Hence, this design makes the analysis of a small number of particles impossible. In addition particles lost in the dead volume after detection make this design unsuitable for particles dispensing.

GENERAL DESCRIPTION OF THE INVENTION

The present invention solves the problems mentioned in the previous chapter.

The invention concerns a sensing tip and uses as defined in the claims.

In the sensing tip according to the invention, the sensing area is located within the tip aperture, at the frontier with the external fluid, which results in the absence of any dead volume. Thus, each single particle flowing inside or outside of the tip can be detected. Such a configuration may be advantageously used for analyzing and dispensing single particles

DETAILED DESCRIPTION OF THE INVENTION

The invention will be better understood in the present chapter, by way of non-limiting illustrated examples.

REFERENCE NUMERALS USED IN THE FIGURES

Figure 1:
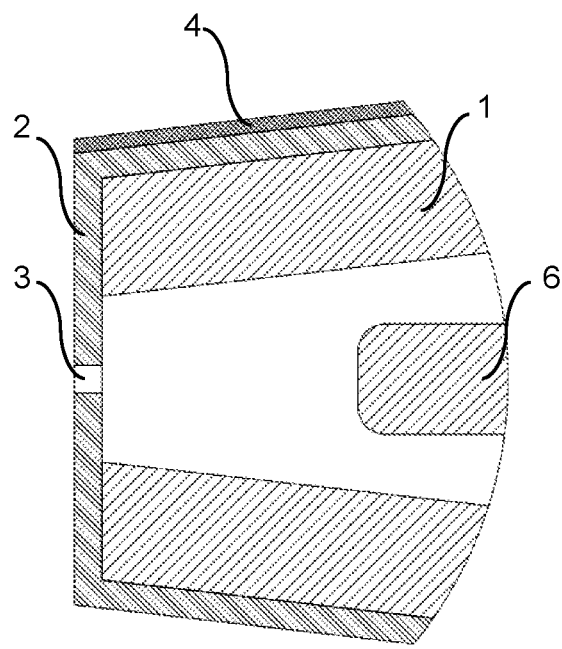
FIG. 1: Cross sectional view of the extremity of a sensing tip according to the invention (wire inner electrode mode)
Figure 2:
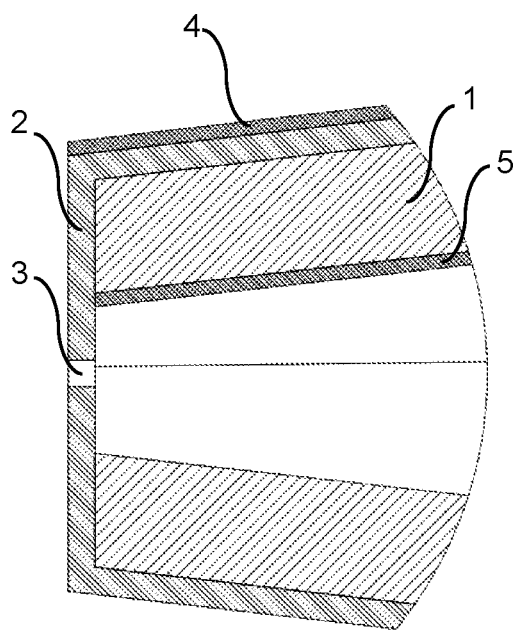
FIG. 2: Cross sectional view of the extremity of another tip according to the invention (thin film inner electrode mode)

1 conventional tip
2 dielectric membrane
3 aperture
4 external electrode
5 internal electrode
6 wire internal electrode (optional mode)
7 instrument
8 sensing tip
9 solution
10 screen
11 circular hole
12 slotted hole Tip Structure The sensing tip illustrated in the examples of FIGS. 1 and 2 includes a conventional tip 1 covered with a dielectric membrane 2 at the tip distal end. The membrane 2 is provided with an aperture 3. An outer electrode 4 is placed on the membrane and an inner electrode 5 (FIG. 2) or 6 (FIG. 1) is located within the conventional tip 1.

Figure 4:
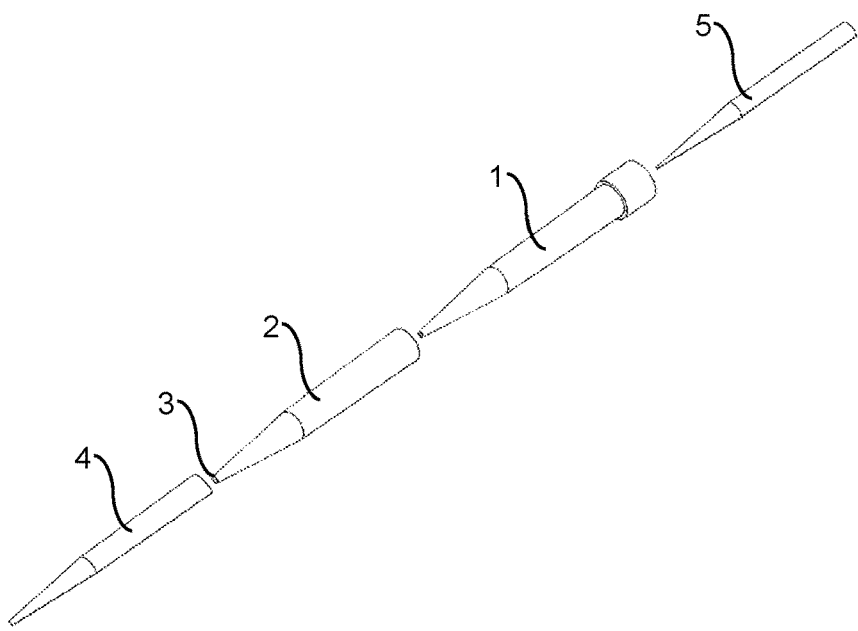
FIG. 4: A first exploded view of a sensing tip according to the invention
Figure 5:
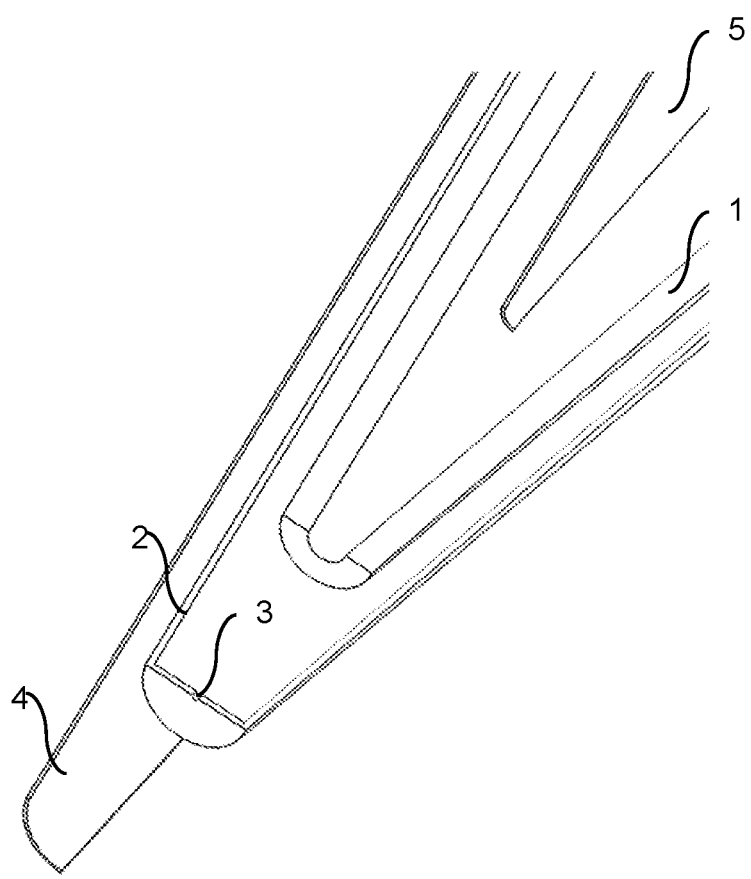
FIG. 5: A second exploded view of the tip of FIG. 4

Exploded views of those sensing tips are illustrated on FIGS. 4 and 5.

The electrodes 4 and 5 are used to establish a determined electric field. In a conductive medium, for instance a solution containing particles (e.g. cells), a current flows between the inner (5,6) and the outer (4) electrodes. Because of this design both current and particles are forced to flow through the aperture 3. As a consequence, the current is mostly influenced by the particle in the aperture 3 according to coulter counter principle. Knowing the electrical field and measuring the current, impedance spectroscopy or coulter counting can be performed on the particles in the aperture 3. For this purpose a time-resolved impedance analyzer is connected to the electrodes 4 and 5 or alternatively 4 and 6. Hence dielectric and structural properties of the particle in the aperture 3 can be measured.

The design of the aperture 3 must be fine-tuned with respect to the particle to be analyzed.

In particular, it is best to adapt the diameter of the aperture 3 to the particle diameter to avoid clogging while maximizing signal-to-noise ratio.

It is best to adapt the membrane 2 thickness to maximize time-of-travel of the particle in the aperture 3 while maximizing the signal-to-noise ratio.

Electrodes 4, 5 or 6 should have a sufficient area to maintain the current at the frequency of interest for the measure.

Electrode 4, 5 or 6 can be attached to the structure or can be left floating. However, it is best to work with electrode 4, 5 or 6 as close as possible to the aperture 3 as it allows to work with a minimal wetting of the tip.

Tip Fabrication

Using a membrane 2 allows to better control the aperture 3. The membrane 2 is preferably coated on the conventional tip 1 distal end using standard chemical vapor deposition (CVD) process. The coating is a pinhole-free and conformal polymer (such as poly(p-xylylene with tradename Parylene). It is deposited with accurate thickness ranging from 50 nm to 1 mm depending on the application. A biocompatible polymer is used to handle biological sample (Parylene USP class VI). Prior to chemical vapor deposition, tip 1 is filled with a sacrificial plug. The plug is made of a soluble polymer, for instance poly(ethylene-glycol) which is soluble in water. After CVD, the polymer closes the opening of the tip. The plug is dissolved in solvent. Thus, the polymer forms a membrane that closes tip 1. Alternatively, membrane 2 is made of a polymer material which is bonded to tip 1, for instance by ultrasonic welding or other chemical bonding. Alternatively, tip 1, membrane 2 and aperture 3 are molded as a single element.

An aperture 3 is opened through membrane 2 at the extremity of tip 1. This process is performed by laser ablation, punching, etching or drilling. The diameter of aperture 3 ranges from 50 nm to 1 mm.

Figure 6:
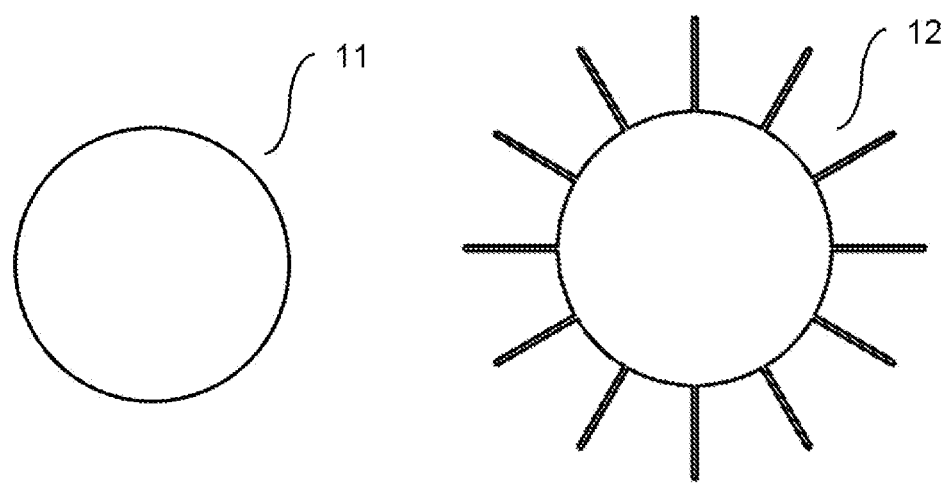
FIG. 6: A specific shape of the aperture allowing for the automatic unclogging

The aperture 3 may be a simple circular hole 11 or may be formed by more complex shapes such as a slotted hole 12 to prevent the aperture 3 from clogging (see FIG. 6).

Electrodes are deposited inside and outside the conventional tip 1 in order to enable the creation of an electric field trough aperture 3. The inner and outer electrodes are made of metal or conductive material deposited on the surface of tip 1 by sputtering or any other deposition method. The inner electrode can also be a conductive wire 6.

Instrument

Figure 3:
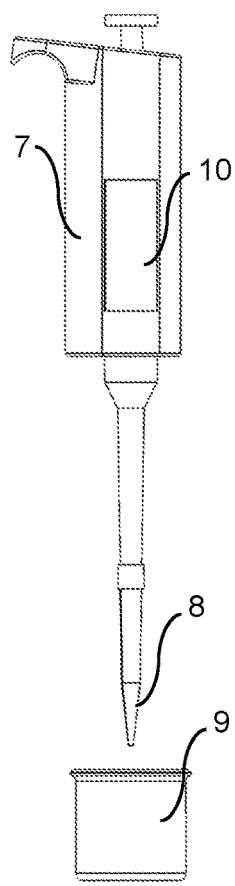
FIG. 3: Pipette operating with a sensing tip according to the invention

The sensing tip 8 may be coupled with an instrument (see FIG. 3) that is arranged to connect to the proximal end of the tip 8. The instrument is composed at least of a fluidic apparatus, an electrical impedance analyzer and a control unit. The fluidic apparatus controls the flow of the liquid inside the tip, which may be stopped, flowed inside or flowed outside the tip. The electrical impedance analyzer measures the impedance provided by the sensor of the sensing tip. The control unit communicates with the electrical impedance analyzer and the fluidic apparatus. The control unit interprets the data sent by the electrical impedance analyzer and in response controls the fluidic apparatus. The control unit may have a user-interface to receive orders from the user and it may transfer the data on a display screen and/or to a computer for further analysis. The instrument can be as example an adapted pipette, multi-pipette or pipetting robot as well as any other instrument including the functions mentioned above.

Examples of Use

In a preferred embodiment, the sensing tip 8 is used to take up a controlled set of particles within in a solution 9. When passing the sensor, particles are counted and analyzed in term of number and size. Dielectric and structural properties of biological samples are analyzed to assess cell viability, membrane properties, granularity and any other relevant biological information. The sensing tip is operated with an instrument 7, such as a pipette as example, including a fluidic system, an embedded electronic and a display 10. The sensing tip is connected to the instrument 7. The tip extremity is immerged in solution 9 containing particles. The user presses a button on the display of the instrument to start taking up the particles in the solution. The fluidic system of the instrument generates a negative pressure that aspirates the particles. Particles flowing in the tip are detected and analyzed by impedance measurement when they pass through the sensor placed at the tip end. Impedance measurements are processed on the instrument and displayed on screen 10. The data can also be transferred on other computers or portable devices.

In another embodiment, the sensing tip is used to dispense a part or all particles previously taken up in a solution according to preferred embodiment. Particle analysis is performed the same way as described in the preferred embodiment. Particle dispensing is performed by first immerging the tip either in initial container 9 or any container with fresh solution. The user presses a button on the display of the instrument to start dispensing the particles. The fluidic system of the instrument generates a positive pressure that flows the particles out. Particles flowing out the tip are detected and analyzed by impedance measurement when they pass through the sensor placed at the tip extremity. Impedance measurements are processed on the instrument 7 and displayed on a screen 10. The data can also be transferred on other computers or portable devices In another embodiment, the sensing tip is used to sequentially dispense a subset or all particles previously taken up in solution 9 according to preferred embodiment. The number of particles to be dispensed is defined by the user. It can dispense as few as a single particle at a time. The particles can be transferred from one container to another container or to other containers with no particle loss during the transfer. Particle dispensing is performed by first immerging the tip either in initial container 9 or any container with fresh solution. This step can be repeated for each new dispensing of particles. The user defines the number of particles to be dispensed at each sequential dispensing. The user presses a button to start dispensing the particles. The fluidic system of the instrument generates a positive pressure that flows the particles out. Particles flowing out the tip are detected and analyzed by impedance measurement when they pass through the sensor. A feedback loop on flow rate stops the dispensing once it reaches the number of particles to be dispensed. Impedance measurements are processed on the instrument and displayed on a screen. The data can also be transferred on other computers or portable devices.

The invention claimed is:

1. A sensing tip having a longitudinal axis, the sensing tip comprises:
   a pipette tip;
   a membrane coated in the pipette tip,
      wherein the membrane has side walls and has a flat dispensing face at a distal end of the pipette tip,
      wherein the flat dispensing face of the membrane is substantially perpendicular to the longitudinal axis of the sensing tip;
   a cavity inside the pipette tip communicates with an external environment of the pipette tip through an aperture that is located in the flat dispensing face of the membrane; and
   an impedance sensor having a sensing area and having at least two electrodes located respectively outside and inside the pipette tip,
      wherein the electrode located inside the pipette tip is not in contact with the side walls of the membrane, wherein the electrode located outside the pipette tip is not in contact with the flat dispensing face of the membrane, wherein the sensing area is arranged within the aperture.

2. The sensing tip according to claim 1, wherein the impedance sensor is adapted to be used as a Coulter counter.

3. The sensing tip according to claim 1, wherein the membrane is made of a different material than a material of the pipette tip.

4. The sensing tip according to claim 3, wherein the flat dispensing face of the membrane includes a dielectric membrane.

5. The sensing tip according claim 1, wherein the aperture is a slotted hole.

6. A method of using a sensing tip, the sensing tip having a longitudinal axis, and the sensing tip comprises a pipette tip, membrane coated on the pipette tip, wherein the membrane has side walls and a flat dispensing face at a distal end of the pipette tip, wherein the flat dispensing face is substantially perpendicular to the longitudinal axis of the sensing tip, a cavity communicating with an external environment of the pipette tip through an aperture located in the flat dispensing face of the membrane, and an impedance sensor having a sensing area including at least two electrodes located respectively outside and inside the pipette tip, the electrode inside the pipette tip not being in contact with the side walls of the membrane, and the electrode outside the pipette tip not being in contact with the flat dispensing face of the membrane, and wherein the sensing area is within the aperture, the method comprising the step of:

detecting particles within a liquid flowing through the aperture within the sensing area at a single-particle resolution to determine at least one of number and size of the particles.

7. The method according to claim 6, further comprising the step of:

assessing at least one of cell viability, membrane properties, and cell properties of the particles.

8. The method according to claim 6, further comprising the step of:

analyzing a particle density on the particles or a subset of particles.

9. The method according to claim 6, further comprising the step of:

detecting a control set of cells within a solution of particles.

10. The method according to claim 6, further comprising the step of:

sequentially dispensing a subset of cells previously taken up in a solution of particles.

11. The method according to claim 6, wherein a set of cells or subset of cells is composed of a single particle.

12. The method according to claim 6, further comprising the step of:

sequentially dispensing a set or a subset of particles with a resolution of single particle.

13. The sensing tip according to claim 3, wherein the external electrode is located on a side wall of the membrane.

14. The method according to claim 6, wherein the external electrode is located on a side wall of the membrane.

15. The sensing tip according to claim 1, wherein the electrode inside the pipette tip is floating.

16. The method according to claim 6, wherein the electrode inside the pipette tip is floating.

* * * * *